(12) United States Patent
El-Nokaly et al.

(10) Patent No.: US 7,249,603 B2
(45) Date of Patent: Jul. 31, 2007

(54) METHOD FOR MEASURING ACUTE STRESS IN A MAMMAL

(75) Inventors: Magda El-Nokaly, Cincinnati, OH (US); Michael Lee Hilton, Fairfield, OH (US); Daniel Raymond Schaiper, Hamilton, OH (US); Fernando Benvegnu, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 385 days.

(21) Appl. No.: 10/937,008

(22) Filed: Sep. 9, 2004

(65) Prior Publication Data

US 2005/0054904 A1    Mar. 10, 2005

Related U.S. Application Data

(63) Continuation-in-part of application No. 10/405,378, filed on Apr. 2, 2003.

(60) Provisional application No. 60/369,678, filed on Apr. 3, 2002.

(51) Int. Cl.
*A61B 19/00* (2006.01)
(52) U.S. Cl. .......................... 128/898; 600/26
(58) Field of Classification Search ........ 128/897–898; 600/26–28, 300–301
See application file for complete search history.

(56) References Cited

U.S. PATENT DOCUMENTS

| 6,102,847 A | 8/2000 | Stielau |
| 2003/0236451 A1 | 12/2003 | El-Nokaly et al. |

FOREIGN PATENT DOCUMENTS

| CA | 1276888 | 11/1990 |
| JP | HEI 11-19076 | 1/1999 |

OTHER PUBLICATIONS

Friedlander, L., et al., "Testing the alexithymia hypothesis: physiological and subjective responses during relaxation and stress," *The Journal of Nervous and Mental Disease*, vol. 185, No. 4, Apr. 1997, pp. 233-239.
Wilken, J. A., et al., "Trait anxiety and prior exposure to non-stressful stimuli: effects on psychophysiological arousal and anxiety," *International Journal of Psychophysiology*, vol. 37, No. 3, Sep. 2000, pp. 233-242.
Kirschbaum, Clemens, et al., "Salivary Cortisol in Psychobiological Research: An Overview," Biological Psychology/Pharmacopsychology, Neuropsychobiology 1989:22:150-169.
Heuberger, Eva, et al., "Effects of Chiral Fragrances on Human Autonomic Nervous System Parameters and Self-evaluation", Chem. Senses 26:281-292, 2001.
Vernet-Maury, Evelyne, et al., "Basic emotions induced by odorants: a new approach based on autonomic pattern results," Journal of the Autonomic Nervous System, vol. 75, 1999, pp. 176-183.
Diego, Miguel A., et al., "Aromatherapy Positively Affects Moods, EEG Patterns of Alertness and Math Computations," International Journal of Neuroscience, vol. 96, 1998, pp. 217-224.
Matthews, Gerald, et al., "Refining the measurement of mood: The UWIST Mood Adjective Checklist", British Journal of Psychology, 1990, vol. 81, pp. 17-42.
Mehrabian, Albert, "Framework for a Comprehensive Description and Measurement of Emotional States", Genetic, Social, and General Psychology Monographs, 1995, vol. 121 (3), pp. 339-361.
Desmet, Pieter, "Designing Emotions", 2002.

*Primary Examiner*—John P. Lacyk
(74) *Attorney, Agent, or Firm*—Frank Taffy; Kenya T. Pierre

(57) ABSTRACT

A method is provided to quantify and/or qualify psychological and physiological components of stress in mammals, in which a stimulus can be applied to the test subject's environment during the test. The method involves the steps of measuring one or more physiological and/or psychological characteristics before and after the administration of a stimulus to a test subject. The stimulus may consist of any product, task, aroma or the like that elicits a stress-related response upon administration. By analyzing the resulting measurements, and optionally comparing physiological and psychological characteristics where both are measured, an overall level of stress may be determined. The method of stress measurement may further be used in product development and/or testing.

9 Claims, No Drawings

US 7,249,603 B2

METHOD FOR MEASURING ACUTE STRESS IN A MAMMAL

CROSS REFERENCE TO RELATED APPLICATIONS

This application is a continuation in part of U.S. Nonprovisional application Ser. No. 10/405,378 filed on Apr. 02, 2003, which claims the benefit of U.S. Provisional Application Ser. No. 60/369,678, filed Apr. 3, 2002.

TECHNICAL FIELD

The present invention relates generally to stress measurement methodologies. Specifically, the present invention is directed to a method that allows for the rapid qualitative and quantitative measurement of the physiological and psychological effects of various stimuli (e.g., aromas, products, tasks and other influences) on stress (e.g., emotions, moods, feelings) in mammals.

BACKGROUND OF THE INVENTION

Stress has been, and still is, a difficult thing to measure. One difficulty in measuring stress comes directly from the lack of a concise definition for stress. One definition of stress is: "Stress is the non specific response of the body to any demand." (Hans Selye, "Stress without Distress," published by Philadelphia: Lippincott, 1974.) Another difficulty in measuring stress is in its diagnoses. Stress is difficult to diagnose because it reveals itself by a constellation of common symptoms with varying degrees of specificity. The symptoms are a function of: the stimulus (demand or pressure), their build up, as well as the individual organism predisposition (weak links).

Examples of common "weak links" and the symptoms of their malfunction include: (1) brain overstress: fatigue, aches and pains, crying spells, depression, anxiety attacks, insomnia, brain shrinkage; (2) gastrointestinal tract: ulcer, cramps and diarrhea, colitis, IBS, thyroid gland malfunction; (3) others: itchy skin rashes, decrease resistance to infections, high blood pressure, heart attack, stroke, etc.

Another difficulty is the complexity of the human stress response. Stress has both psychological and physiological components; measuring only one component is insufficient to provide a complete understanding. To measure stress, "mind and body" both have to be taken into consideration, as there is no psychological event without a resulting somatic (bodily) event and vice versa. Stress response varies greatly between individuals. One person, for instance, may display large changes in electrodermal activity with increased stress and show only moderate changes in heart rate and peripheral blood flow volume, while another individual may show the reverse pattern.

Stress is rather ambiguous and ill-defined. There is no standard definition of stress and, consequently, there are no widely accepted standards for measuring stress. One reason for this is that every person's psychological and physiological response to stress is different and can change over time. The magnitude of aromatheraputic effects is probably small, making them difficult to isolate. There is much scientific evidence that a person's physiological reaction to an odorant may depend on their psychological response to the odorant, i.e., whether or not the person likes the odor. Animal studies by Buchbauer indicate that only specific varieties of essential oils—indeed, in some cases only specific enantiomers of fragrance molecules—produce an aromatheraputic effect. This could explain some of the contradictory findings in the scientific literature regarding aromatherapy. A generic lavender, for instance, might not contain the correct amounts, proportions, or chemical species of the various components which are needed to produce an effect.

In commonly assigned U.S. patent application Ser. No. 10/405,378 filed on Apr. 02, 2003, there is disclosed a methodology and apparatus for testing and evaluating acute stress levels of human test subjects by acquiring both physiological and psychological information during alternating periods of stress and relaxation. The methodology and apparatus disclosed therein also entail the acquisition of physiological and psychological information while subjecting the test subjects to a stimulus, such as a fragrance, flavor, or product, or while the test subjects are performing an activity or task. Further, the application describes the evaluation of acute stress levels of human test subjects by acquiring physiological data from biosensors, such as EKG and blood volume pulse (BVP) sensors, and by acquiring psychological data from questionnaires.

A primary advantage of the invention disclosed in commonly assigned U.S. patent application Ser. No. 10/405,378 is that both psychological and physiological measurements are simultaneously taken and assessed, which provides a much more accurate measure of a person's acute stress level by taking into account both body and mind (body/mind) interactions. The methods and apparatuses disclosed in said application can be used for many purposes, but at least provides certain scientific quantifications of the psychological and physiological parameters, which have not been available in the past testing or relaxation-determinative procedures. Another important aspect of the invention disclosed in commonly assigned U.S. patent application Ser. No. 10/405,378 is that the physiological and psychological factors are taken in a non-invasive manner, which is a huge advantage as compared to taking blood, urine or saliva samples.

Despite having provided a substantial solution to contemporary issues associated with the measurement of an acute stress in a mammal via an assessment of psychological and physiological characteristics, there remains a need in the art to identify an abbreviated method for measuring acute stress in a mammalian subject. Such a method should facilitate the rapid assessment of the level of acute stress in a mammalian subject, with or without the use of computers or other computational tools.

SUMMARY OF THE INVENTION

The present invention addresses and resolves contemporary issues associated with stress measurement in a mammalian test subject by providing a method by which acute stress may be rapidly assessed. Thus, in accordance with a first aspect of the present invention, a method of determining relative stress level in a mammalian subject is provided. Said method comprising the steps of: determining a first (i.e., baseline) physiological stress level of the subject; administering one or more stimuli (e.g., product, task, aroma) to the subject, wherein said stimuli are intended to cause a change in the stress level of the subject; determining a second physiological stress level of the subject; and comparing said first physiological stress level and said second physiological stress level to determine the stress level of the subject. In another aspect of the present invention, the above-mentioned step of determining the stress level of a subject may be performed on a mammal. In another aspect of the present invention, the mammalian subject may be selected from the group consisting of: humans, cats, dogs, other domesticated animals and combinations thereof. In a particularly preferred aspect of the present invention, the level of stress in a mammalian subject may be assessed via measurement of one or more physiological characteristics of the mammalian test subject under consideration. As will be described more thoroughly hereinafter, said physiological characteristics may include, yet are not limited to: heart period, pulse transit time, peripheral blood flow, standard deviation of normal to normal beats (SDNN) and combinations thereof. In yet another aspect of the present invention, the level of stress in the mammalian subject may be assessed via the measurement of one or more psychological characteristics.

In one aspect of the present invention, one or more psychological characteristics of the mammalian subject under consideration may be measured via the administration of a questionnaire to said subject, wherein one or more answers to questions from said questionnaire are designed to evaluate at least one psychological component of acute stress. Suitable questionnaires for purposes of the present invention include those which may be administered to the mammalian subject under consideration in a rapid manner to facilitate the swift assessment of the overall level of stress in said mammalian subject. In yet still other aspects of the present invention, the level of acute stress in a mammalian test subject may be assessed via measurement of one or more physiological characteristics and one or more psychological characteristics, the combination of which may be analyzed to determine an overall level of stress in said mammalian subject, as described more fully hereinafter.

One advantage of the present invention is that the acute stress level of a mammalian subject may be assessed in a swift and accurate manner. Those skilled in the art to which the subject invention pertains will appreciate that the level of acute stress in a mammal is subject to rapid change, and thus, instantaneous measurement is requisite to the provision of meaningful stress level results for any given moment. The methods of the present invention are designed to quickly facilitate the measurement of acute stress in a mammalian subject, and thus, provide the practitioner of the present methods with measurements that more accurately reflect the level of stress in a mammal at the moment at which measurement of stress is intended. The accuracy of the methods disclosed herein is further bolstered via the simultaneous measurement of both psychological and physiological characteristics of a mammalian subject. Of course, another important aspect of the present invention is that the level of acute stress in a mammalian subject is measured in a non-invasive manner (particularly in comparison to blood, urine or saliva samples), thereby increasing the likelihood that a mammalian subject will subject themselves to administration of the present methods (particularly for consumer research purposes).

Still other advantages of the present invention will become apparent to those skilled in the art to which the present invention pertains from the following description wherein there is described and shown a preferred embodiment of this invention in one of the best modes contemplated for carrying out the invention. As will be realized, the invention is capable of other different embodiments, and its several details are capable of modification in various, obvious aspects all without departing from the invention. Accordingly, the descriptions will be regarded as illustrative in nature and not as restrictive.

All documents cited are, in relevant part, incorporated herein by reference; the citation of any document is not to be construed as an admission that it is prior art with respect to the present invention.

DETAILED DESCRIPTION OF THE INVENTION

Definitions

As used herein, the term "fragrance" is intended to refer to a type of "stimulus" that could either be relaxing or stimulating, or perhaps could have no perceivable effect on a person. The terms "fragrance" or "stimulus" can be interchanged in most cases, with respect to the principles of the present invention. Furthermore, the term "fragrance" can literally represent an actual fragrance (e.g., in a liquid state) or an odor (e.g., in a gaseous state), or the term "fragrance" can represent a flavor (such as in a beverage). The term "fragrance" can also represent essential oils, an aroma or scent. A "fragrance" can be subliminal (at a concentration too low to be consciously detected by a human) or non-subliminal (at a concentration high enough to be consciously detected by a human). Finally, the terms "fragrance" or "stimulus" can alternatively represent some type of "product" or could represent a "task."

As used herein, the term "stimulus" is intended to refer to any type of object, product or task that appeals to any of the five senses (e.g., smell, touch, hearing, taste, sight). In the case of an object or product, a stimulus may include an aroma or an essential oil, among others.

In the case of a "product," the terms fragrance/stimulus could represent a perfume or a cologne, for example, or some other complex formulation (e.g., a mixture of two or more perfumes); or some type of therapeutic device or medical device, for example, such as hot towels, or chemically-activated heat-releasing wraps such as those under the registered trademark THERMACARE® heat wraps, owned by The Procter & Gamble Company.

In the case of a "task," the terms fragrance/stimulus could represent some activity that may be relaxing, such as a person taking a hot shower, or cleaning, or washing dishes or clothing, ironing, or performing some other ergonometrically-designed tasks to relieve stress. Further details of some of these examples are discussed below.

The term "product" is intended to refer to, among others, one or more beauty and/or hair care products such as soaps, shower gels, shampoo, conditioners, personal cleansing; fine fragrances or colognes; home care products, such as dishwashing products, air fresheners, softeners, tissues, and towels; baby care products, such as diapers, and wipes; feminine care products, such as PMS products, or products for menopause. Other products could also include over the counter items, such as toothpaste, VAPO-RUB® ointment, and cough syrups. Particularly preferred products for purposes of the present invention include those marketed by The Procter and Gamble Company of Cincinnati, Ohio.

The terms "subject," "test subject," "mammalian subject," and "mammalian test subject" are intended to refer to a mammal to which the methods of the present invention may be administered to elicit a meaningful, stress-related measurement. Suitable mammals for use in the context of the present invention include: humans and domesticated animals, such as cats and dogs.

First Aspect: Method of Determining Relative Stress in a Subject

In accordance with a first aspect of the present invention, a method of determining relative stress level in a subject is provided. Said method comprises the steps of: determining a first (i.e., baseline) physiological stress level of the subject; administering one or more stimuli (e.g., product, task, aroma) to the test subject, wherein said stimulus is intended to cause a change in the stress level of the subject; determining a second physiological stress level of the subject; and comparing said first physiological stress level and said second physiological stress level to measure the overall stress level of the test subject.

In accordance with this aspect of the present invention, a first physiological stress level of the test subject may be determined by measuring one or more physiological characteristics of the subject (described infra). In another aspect of the present invention, the first physiological stress level may be measured by using the stress measurement apparatus disclosed in commonly-assigned U.S. Provisional Application Ser. No. 60/369,678, filed Apr. 3, 2002. As will be described more thoroughly hereinafter, said physiological characteristics may include, yet are not limited to: heart period, pulse transit time, peripheral blood flow, standard deviation of normal to normal beats (SDNN) and combinations thereof.

Upon determining the first physiological stress level of the subject, a stimulus (e.g., product, task or aroma) may be administered to the test subject. As described in the "Definitions" section of the present disclosure, the term "product" for purposes of the present invention is intended to encompass any product, commercial other otherwise, that causes any perceivable change in the stress level of a test subject. Particularly preferred products for purposes of the present invention include those that appeal to the senses of smell (e.g., perfumes, colognes, aromas) and touch (i.e., hot towels, heating pads). In another aspect of the present invention, particularly preferred products for purposes of the present invention include those marketed by The Procter and Gamble Company of Cincinnati, Ohio, as well as products marketed by others that are part of the same product category as those products marketed by The Procter and Gamble Company.

In yet still another aspect of the present invention, the stimulus administered to the test subject may include a task. Indeed, the test subject may engage in the completion of a task following measurement of the first physiological stress level of the subject. As described in the "Definitions" section of the present disclosure, the term task is intended to refer to virtually any task that elicits a stress-related response in a test subject. Tasks suitable for use in the context of the present invention include, without limitation, relaxation and/or cleaning. In one aspect of the present invention, the acute stress level of a mammalian subject may be ascertained while said subject is performing a task selected from the group consisting of taking a shower, cleaning, washing dishes, washing clothing, ironing clothing and other household-related activities. In yet still another aspect of the present invention, a test subject may be subjected to the use a product and the completion of a task simultaneously, upon measurement of the first physiological stress level. In one aspect of the present invention the task for which completion is intended during use of the product may indeed be associated with the intended use of the product. For example, a test subject may use a product such as the Swiffer Wet Jet™ floor-cleaning device, marketed by The Procter and Gamble Company of Cincinnati, Ohio, to engage in a task such as cleaning a kitchen floor. While physical tasks may, in and of themselves, be relaxing or stressful, with the present invention it is nevertheless possible to also determine if a fragrance (or "stimulus") adds or subtracts any further component of relaxation to a person's acute stress state.

In yet still another aspect of the present invention, the stimulus of the present invention may be characterized based on the level of exertion associated with administration to the test subject. For example, a stimulus such as a product, fragrance or aroma, the administration of which requires little to exertion on the part of the test subject may be characterized as a "passive stimulus." Conversely, a stimulus such as an activity or task, the administration of which requires active exertion and/or effort on the part of the test subject may be characterized as an "active stimulus." The methods of the present invention seek to encompass the measurement of stress following the administration of virtually any stimulus, whether passive, active or both.

Upon administering one or more stimuli to the test subject, a second physiological stress level may be measured. The second physiological stress level may be similarly assessed by measuring one or more physiological characteristics, as described hereinafter. Upon ascertaining both the first (baseline) and second physiological stress levels, a comparison may be made between the two levels to provide an overall assessment of the level of stress of the test subject following administration of the product. In one aspect of the present invention, the first and second stress levels are simply compared to determine the relative change in stress level following the administration of one or more stimuli. In another aspect of the present invention, the first and second physiological stress levels are compared by assigning a numerical value to each of the overall physiological and psychological measurements. In one aspect of the present invention, the same method may be used to assign quantitative values to the both the physiological and psychological measurements such that the two measurements may be accurately compared. In another aspect of the present invention, the individual numerical values for each of the physiological and psychological characteristics may be merged into a single numerical value to provide an overall quantitative assessment of both the physiological and psychological characteristics of the test subject. In one aspect of the present invention, the overall numerical value assigned to the combined physiological and psychological characteristics may be assigned a qualitative label based on the overall numerical value. For example, a product may be assigned a qualitative label of "Strongly Relaxing" if the ratio of the physiological and psychological characteristics is between 0.0 and 0.5. The term "ratio" is intended to refer to the absolute ratio between a given physiological characteristic and a psychological characteristic. The term "ratio" is also intended to refer to the level of change in a given physiological or psychological characteristic upon being exposed to a stimulus, in which case the ratio may be the level of stress in the subject prior to administration of a stimulus over the level of stress following administration of the stimulus. In yet another aspect of the present invention, a mathematical function that merges the individual physiological and psychological characteristics into a single number may be used to provide an overall assessment of the level of acute stress in the test subject under consideration. Non-limiting examples of mathematical functions suitable for use in the context of the present invention include regression analysis, among others.

Suitable physiological characteristics suitable for quantifying stress in the context of the present invention, include but certainly are not limited to heart period, pulse transit time, peripheral blood flow, standard deviation of normal to normal beats (SDNN) and combinations thereof. In yet another aspect of the present invention, other non-invasive measurements could be used in addition to, or in lieu of, one or more of the above parameters. Other non-invasive measurements may include, but certainly are not limited to muscle relaxation, skin temperature, skin conductivity measurements, pupil dilation, salivary flow, capillary dilation, bronchi constriction, stomach motility and combinations thereof.

With regard to the above-noted four physiological measures, the "heart period" is the length of time between heartbeats, which is the inverse of the heart rate. An increase in heart period generally means a reduction in stress. The "pulse transit time" is the amount of time it takes for a bolus of blood squeezed from the heart to reach the fingertip; it is an inverse analog of blood pressure. An increase in pulse transit time generally means a reduction in stress. The "peripheral blood flow" is a measure of how much blood is flowing in capillaries near the surface of the skin. When a person is under stress, the sympathetic nervous system constricts the capillaries in the skin to shunt blood to the muscles in preparation for fight or flight. An increase in peripheral blood flow generally means a reduction in stress. The SDNN is a measurement of heart rate variability, and is the standard deviation of the period of time between two normal heartbeats. Most persons believe that the human heart beats at a steady pace (under constant workload); however, the time between beats for a healthy heart will vary quite a bit (in the range of milliseconds for the variations). When under stress, the variation decreases; thus an increase in SDNN generally means a reduction in stress.

In yet another aspect of the present invention, the level of stress in the mammalian subject may be assessed via the measurement of one or more psychological characteristics of the mammalian test subject. Indeed, in one aspect of the present invention, a one or more psychological characteristics of the mammalian test subject are measured via the administration of a questionnaire to said subject, wherein one or more answers to questions from said questionnaire are designed to evaluate at least one psychological characteristic. Any suitable questionnaire may be administered in accordance with the present invention. Suitable questionnaires include The Mood Adjective Check List (MACL) of the University of Wales Institute of Science and Technology; the abbreviated Mehrabian PAD scale; and Desmet's PREMO instrument. Particularly preferred questionnaires for purposes of the present invention include those which may be administered in less than five minutes, preferably less than two minutes, more preferably less than one minute, most preferably 20 seconds. Suitable questionnaires for use in the context of the present invention may be provided in both oral and/or written form. Other questionnaires suitable for use in the context of the present invention are described in the following references: (1) Matthews, Gerald, Dylan M. Jones, and A. Graham Chamberlain. *Refining the Measurment of Mood: The UWIST Mood Adjective Checklist*. British Journal of Psychology, 1990, Vol. 81, pp. 17-42; (2) Mehrabian, Albert. *Framework for a Comprehensive Description and Measurement of Emotional States*. Genetic, Social, and General Psychology Monographs, 1995, Vol. 121 (3), pp. 339-361; and (3) Desmet, Pieter. *Designing Emotions*. PhD Dissertation 2002, Technical University of Delft, Netherlands.

Second Aspect: Method of Developing Product, Task and/or Aroma

In yet another aspect of the present invention, a method for evaluating and/or developing a stimulus (e.g., product, task, aroma) is provided. In one aspect of the present invention, said method comprises the step of using the method disclosed in the First Aspect of the present disclosure to further develop and/or evaluate a product, task or aroma to which the test subject is exposed. In one aspect of the present invention, the psychological and/or physiological measurements obtained from one or more test subjects upon being exposed to the same product, task or aroma are compared to subsequent measurements to determine the overall level of stress related to administration of the product task or aroma to the test subjects. In another aspect of the present invention, one or more of the characteristics of a product, task, aroma or other stimulus may be modified and/or altered upon measurement of stress following its administration to one or more test subjects, to elicit a desired stress-related response. For example, if a qualitative stress-related response of "relaxing" is desired and a fragrance is used to elicit a stress-related response, then the composition or concentration of a fragrance may be altered accordingly. Those skilled in the art to which the present invention relates will appreciate that the precise adjustment or alteration made to the product, task or aroma will depend upon several factors, including, but not limited to: the nature of the stimulus under consideration and the needs and/or abilities of the practitioner.

EXAMPLES

Example 1

Fragrance Administration

The Aroma Therapy Stress Measurement Protocol (or ASMP) experiment is designed to test three fragrances and one control (e.g., water). The blank is usually considered essential, because it provides the baseline stress/relaxation response that the fragrances will be compared to. The fragrances should be diluted to a strength that is appropriate to the purpose of the experiment and, if possible, to similar perceived strengths. If an olfactometer is available, it can be used to administer the fragrances. Otherwise, the fragrances can be presented to the test subject by saturating equal-sized strips of filter paper with the fragrance and placing the filter paper in an open wide-mouth jar placed approximately 30 centimeters from and level with the test subject's chin. The room in which the experiment is conducted should be designed for high air turnover (at least eight complete air changes per hour is recommended) or, at a minimum, have a fume hood.

Example 2

Assignation of Qualitative Labels to Stress Measurements

Qualitative labels may be assigned to both the stress measurements obtained using the method of the present invention. In qualitatively analyzing a measurement, for example the measurement of a physiological characteristic, a qualitative label may be assigned to the measured stress level depending upon the ratio of the first stress measurement and second stress measurement. Namely, if a first stress measurement, for example peripheral blood flow, was determined to be 0.42 and a second stress measurement was determined to be 0.84, then a qualitative label of "Strongly Relaxing" may be assigned to the measurement. Assignation of qualitative labels for combined measurements may be done in accordance with the following table:

| Ratio of First Physiological Stress Measurement and Second Physiological Stress Measurement | Combined Qualitative Label Assigned |
| --- | --- |
| 0.0 < ratio < 0.5 | Strongly relaxing |
| 0.5 < ratio < 0.9 | Relaxing |
| 0.9 < ratio < 1.0 | Mildly relaxing |
| 1.0 | No effect |
| 1.0 < ratio < 1.1 | Mildly stimulating |
| 1.1 < ratio < 1.5 | Stimulating |
| Ratio >= 1.5 | Strongly stimulating |

Example 3

Quantitative Analysis of Stress Measurements

The physiological and psychological measurements obtained via practice of the methods disclosed herein may be combined and reported as a single, quantitative value. Administration of the psychological questionnaires generates a set of N numbers that describe a person's mood or emotional state. The physiological measurement(s) made during performance of the methods of the present disclosure generate a separate set of M numbers. The combined psychological and physiological measurements form an N+M dimensional space that must be reduced to a single value. A mathematical function is created that combines the N+M inputs into a single number indicating stress level. Such a function could be created by a regression analysis of experimental data.

Example 4

Performance of the Present Methods using only Physiological Characteristics The method of the present invention was performed employing only peripheral blood flow as the physiological measurement. The peripheral blood flow of each test subject was measured prior to administration of a stimulus. Then, a lavender-based stimulus was administered to each subject for a period of 20 seconds. Separately, the peripheral blood flow of each test subject was measured prior to the administration of an herbal-based stimulus. The herbal stimulus was then administered to each subject for a period of 20 seconds. Based upon application of the ratios to the table listed in Example 2 of the present disclosure, it was determined that the lavender fragrance is relaxing to test subjects and the herbal fragrance is stimulating.

| Subject | Lavender Ratio | Herbal Ratio |
|---|---|---|
| 1 | 0.58 | 1.08 |
| 2 | 0.96 | 1.30 |
| 3 | 0.89 | 1.09 |
| 4 | 0.90 | 1.22 |

Example 5

Development of Product Using Present Methods

A laundry group seeks to create a detergent with a relaxing scent that is adapted to promote restful sleep when used on bedding. Three candidate fragrances are developed and tested with the methods of the present invention to determine which is the most relaxing. Three different fragrances are each administered to forty test subjects. The averages of the peripheral blood flow ratios for each fragrance are 0.84, 0.67, and 1.03, respectively. The second fragrance, with an average ratio of 0.67, is the most relaxing of the fragrances. The laundry group decides to use Fragrance Number 2 in the subject laundry detergent.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of determining relative stress level in a subject, said method comprising the steps of:
   determining a first physiological stress level of the subject;
   administering a stimulus to the subject, wherein said stimulus is intended to cause a change in the stress level of the subject;
   determining a second physiological stress level of the subject by measuring the physiological characteristics selected from the group consisting of heart rate, pulse transit time, peripheral blood flow, SDNN, skin temperature, skin conductivity, pupil dilation, salivary flow, capillary dilation, bronchi constriction, stomach motility and mixtures thereof of said subject within about 10 seconds to about 120 seconds of administration of said stimulus; and
   comparing said first physiological stress level and said second physiological stress level to determine the change in stress level of the subject.

2. The method according to claim 1, further wherein said first and second stress levels are psychological stress levels.

3. A method according to claim 1, wherein the steps of determining the stress level of a subject are performed on a human subject.

4. A method according to claim 2, wherein said step of measuring said stress level comprises the administration of a questionnaire to said subject, wherein one or more answers to questions from said questionnaire are designed to evaluate at least one psychological component of acute stress.

5. The method according to claim 4, wherein: said questionnaire comprises a plurality of quick-answer questions that provide a measure of perceived physiological effects of acute stress.

6. The method as recited in claim 5, wherein: answers to said quick-answer questions provide a measure of the test subjects psychological state.

7. A method according to claim 1, wherein said stimulus is selected from the group consisting of: products, commercial products, tasks, tasks relating to the use of a product, aromas and combinations thereof.

8. A method according to claim 7, wherein said product is selected from the group consisting of consumer products, fragrances, aromas, scents, odors, flavors, therapeutic devices, cough syrups, inhalants, toothpastes, lozenges, dental floss and combinations thereof.

9. A method of determining the stress of a subject according to claim 1, wherein the steps of determining said stress is performed in a setting selected from the group consisting of: home setting, retail setting and combinations thereof.

* * * * *